United States Patent
Byrne et al.

(10) Patent No.: US 10,060,891 B1
(45) Date of Patent: Aug. 28, 2018

(54) CONTINUOUS ACID-FREE MEASUREMENTS OF TOTAL ALKALINITY

(71) Applicants: Robert H. Byrne, St. Petersburg, FL (US); Xuewu Liu, Largo, FL (US)

(72) Inventors: Robert H. Byrne, St. Petersburg, FL (US); Xuewu Liu, Largo, FL (US)

(73) Assignee: University of South Florida, Tampa, FL (US)

(*) Notice: Subject to any disclaimer, the term of this patent is extended or adjusted under 35 U.S.C. 154(b) by 0 days.

(21) Appl. No.: 15/436,269

(22) Filed: Feb. 17, 2017

Related U.S. Application Data

(60) Provisional application No. 62/297,441, filed on Feb. 19, 2016.

(51) Int. Cl.
| | |
|---|---|
| *G01N 31/22* | (2006.01) |
| *G01N 21/63* | (2006.01) |
| *G01N 33/18* | (2006.01) |
| *G01N 33/00* | (2006.01) |

(52) U.S. Cl.
CPC .......... *G01N 31/221* (2013.01); *G01N 21/63* (2013.01); *G01N 33/18* (2013.01); *G01N 33/004* (2013.01); *Y10T 436/204998* (2015.01)

(58) Field of Classification Search
CPC .............. G01N 31/221; G01N 21/63; G01N 2021/8405; G01N 33/004; G01N 33/18; Y10T 436/204998; B01J 2219/00966

USPC ................ 436/39, 133, 163, 164, 167, 168; 422/82.05, 82.09

See application file for complete search history.

(56) References Cited

U.S. PATENT DOCUMENTS

| | | | |
|---|---|---|---|
| 7,727,770 B2 | 6/2010 | Byrne | |
| 8,077,311 B1* | 12/2011 | Byrne | ............... G01N 21/05 356/319 |
| 9,347,922 B2* | 5/2016 | Dugstad | ............... G01N 31/00 |
| 2006/0234389 A1* | 10/2006 | Byrne | ............ G01N 21/0303 436/163 |
| 2015/0346178 A1* | 12/2015 | Wang | ............ G01N 33/1886 436/52 |

OTHER PUBLICATIONS

Breland II et al. Analytical Chemistry, vol. 64, 1992, pp. 2306-2309.*

Adornato et al., Development of a Portable Carbon System Sensor for Ocean Acidification Research, IEEE, 2016.

* cited by examiner

*Primary Examiner* — Maureen Wallenhorst
(74) *Attorney, Agent, or Firm* — Thomas | Horstemeyer, LLP

(57) ABSTRACT

A system and method for the substantially continuous measurement of the total alkalinity of a sample solution, which includes, equilibrating a sample solution and a gas at a chosen $CO_2$ fugacity across a gas permeable membrane, measuring the equilibrium pH of the equilibrated solution in an optical cell using a spectrophotometric pH indicator and calculating the total alkalinity of the solution from the equilibrium pH measurement of the solution and a known partial pressure of $CO_2$.

20 Claims, 2 Drawing Sheets

CONTINUOUS ACID-FREE MEASUREMENTS OF TOTAL ALKALINITY

CROSS-REFERENCE TO RELATED APPLICATIONS

This application claims priority to U.S. Provisional Patent Application No. 62/297,441, entitled "Continuous Acid-Free Measurements of Total Alkalinity", filed on Feb. 19, 2016, the contents of which are herein incorporated by reference.

FEDERALLY SPONSORED RESEARCH OR DEVELOPMENT

This invention was made with Government support under Grant No. PLR-1414586 awarded by the National Science Foundation. The government has certain rights in the invention.

FIELD OF INVENTION

This invention relates to systems and methods for the substantially continuous measurement of total alkalinity in liquid samples.

BACKGROUND OF THE INVENTION

Seawater alkalinity, defined as a difference between the excess concentrations of proton acceptors over proton donors in 1 kg of seawater, is one of the important parameters in carbon dioxide systems. Due to its invariance during $CO_2$ gas exchange and biological activity, alkalinity is considered to be a cornerstone in analytical assessments of oceanic $CO_2$ cycling. Anomalies of seawater alkalinity normalized to salinity have been attributed to water mass movement and/or dissolution of calcium carbonate.

Conventional systems and method for measuring seawater alkalinity usually involve acid titration of the bases to carbonic acid end point by either a single step addition or sequential stepwise addition. The multi-step titration method is widely used on shipboard measurements due to its high precision and automated operation. The combined speed and simplicity of single-step titration with spectrophotometric pH determinations for measurement of end point excess acid has been shown. Such methods have greatly improved the precision of alkalinity measurements. However, the end point detection techniques currently known in the art require accurate knowledge of end point pH without the influence of $CO_2$ generated in titration steps and thus usually involve a purge step. Such a step makes the automation of an online instrument difficult. As such, the multipoint volumetric titration method remains the standard procedure for discrete sampling.

The current total alkalinity measurement techniques currently known in the art, such as the multipoint volumetric titration method, are time consuming and as such, do not lend themselves to a continuous analysis of a sample fluid flow.

Therefore, current instrumentation for making total alkalinity measurements is unsuitable for measurements in the field and does not provide for a continuous flow analysis. In addition, the obligatory use of acids in current practice is hazardous and presents shipping problems. As such, equipment currently known in the art for total alkalinity measurements is complex, requires significant user expertise and the resulting sample throughput capability is prohibitively slow.

Accordingly, what is needed in the art is an improved system and method for measuring the total alkalinity of a sample liquid which overcomes the limitations of the prior art systems.

SUMMARY OF INVENTION

In various embodiments, the present invention provides a device and associated method for measuring the total alkalinity (TA) of a liquid sample. The inventive total alkalinity measuring device is smaller in size than conventional devices, is highly portable, is inexpensive relative to conventional devices, is conceptually and operationally simple and does not require the use of strong acids. The system of the present invention provides for the measurement of the total alkalinity of a liquid sample, wherein a substantially continuous measurement of the total alkalinity can be provided by allowing for the measurement of the total alkalinity at a greater frequency than conventional devices.

In one embodiment, the present invention provides a method for determining total alkalinity of a liquid sample. The method includes, introducing a pH indicator into a liquid sample to form a sample solution, and introducing the sample solution into a $CO_2$ gas permeable tube positioned within an interior of an equilibration chamber. The method further includes, introducing a gas mixture comprising $CO_2$ at a known partial pressure, or fugacity, to surround the $CO_2$ gas permeable tube in the equilibration chamber. Following the introduction of the $CO_2$ into the equilibration chamber, the method further includes, allowing the sample solution to equilibrate with the $CO_2$ in the gas mixture until the sample solution is a $CO_2$ equilibrated sample solution having substantially the same partial pressure as the $CO_2$ surrounding the $CO_2$ gas permeable tube in the equilibration chamber. The $CO_2$ equilibrated sample solution is then introduced into an optical cell and the optical cell is used for measuring an absorbance ratio of the pH indicator in the equilibrated sample solution at a plurality of frequencies. The total alkalinity of the liquid sample is then calculated using the absorbance ratio measurements of the pH indicator in the equilibrated sample solution and the known partial pressure of the $CO_2$.

In particular, the total alkalinity of the liquid sample using the absorbance ratio measurements of the equilibrated sample solution and the known partial pressure of the $CO_2$ is calculated according to the equation:

$$\log(TA+[H^+]) = \log(K_0 K_1/K_I) + \log pCO_2 + \log[(R-e_1)/(e_2-Re_3)]$$

where;
$K_0$ is the Henry's law gas solubility constant, $K_1$ is a carbonic acid dissociation constant, $K_I$ is the pH indicator dye dissociation constant, $pCO_2$ is the known partial pressure of the $CO_2$, R is the measured absorbance ratio, and $e_1$ and $e_2$ and $e_3$ are molar absorptivity ratios appropriate to the pH indicator. In a specific embodiment, the pH indicator may be a sulfonephthalein pH indicator and the liquid sample may be seawater.

In an additional embodiment, the present invention provides a system for determining total alkalinity of a liquid sample, which includes, an equilibration chamber, a $CO_2$ gas permeable tube positioned within an interior of an equilibration chamber and a controlled source of a gas mixture comprising $CO_2$ at a known partial pressure coupled to the equilibration chamber. The system further includes, a controlled source of a liquid sample coupled to an input of the $CO_2$ gas permeable tube and a controlled source of a pH indicator coupled to an input of the $CO_2$ gas permeable tube. The system further includes an optical cell coupled to an output of the $CO_2$ gas permeable tube for measuring an absorbance ratio of a pH indicator in an equilibrated sample solution, provided at the output of the equilibration chamber, at a plurality of frequencies and a processing device for calculating a total alkalinity of the liquid sample using the absorbance ratio measurements of the pH indicator in the equilibrated sample solution.

In particular the processing device further includes software for calculating the total alkalinity of the liquid sample using the absorbance ratio measurements of the pH indicator in the equilibrated sample solution and the known partial pressure of the $CO_2$ according to the equation:

$$\log(TA+[H^+])=\log(K_0 K_1/K_I)+\log pCO_2+\log[(R-e_1)/(e_2-Re_3)]$$

where;
$K_0$ is the Henry's law gas solubility constant, $K_1$ is a carbonic acid dissociation constant, $K_I$ is the pH indicator dye dissociation constant, $pCO_2$ is the known partial pressure of the $CO_2$, R is the measured absorbance ratio, and $e_1$ and $e_2$ and $e_3$ are molar absorptivity ratios appropriate to the pH indicator.

Accordingly, the present invention provides an improved system and method for measuring the total alkalinity of a sample liquid which overcomes the limitations of the prior art systems.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Figure 1:
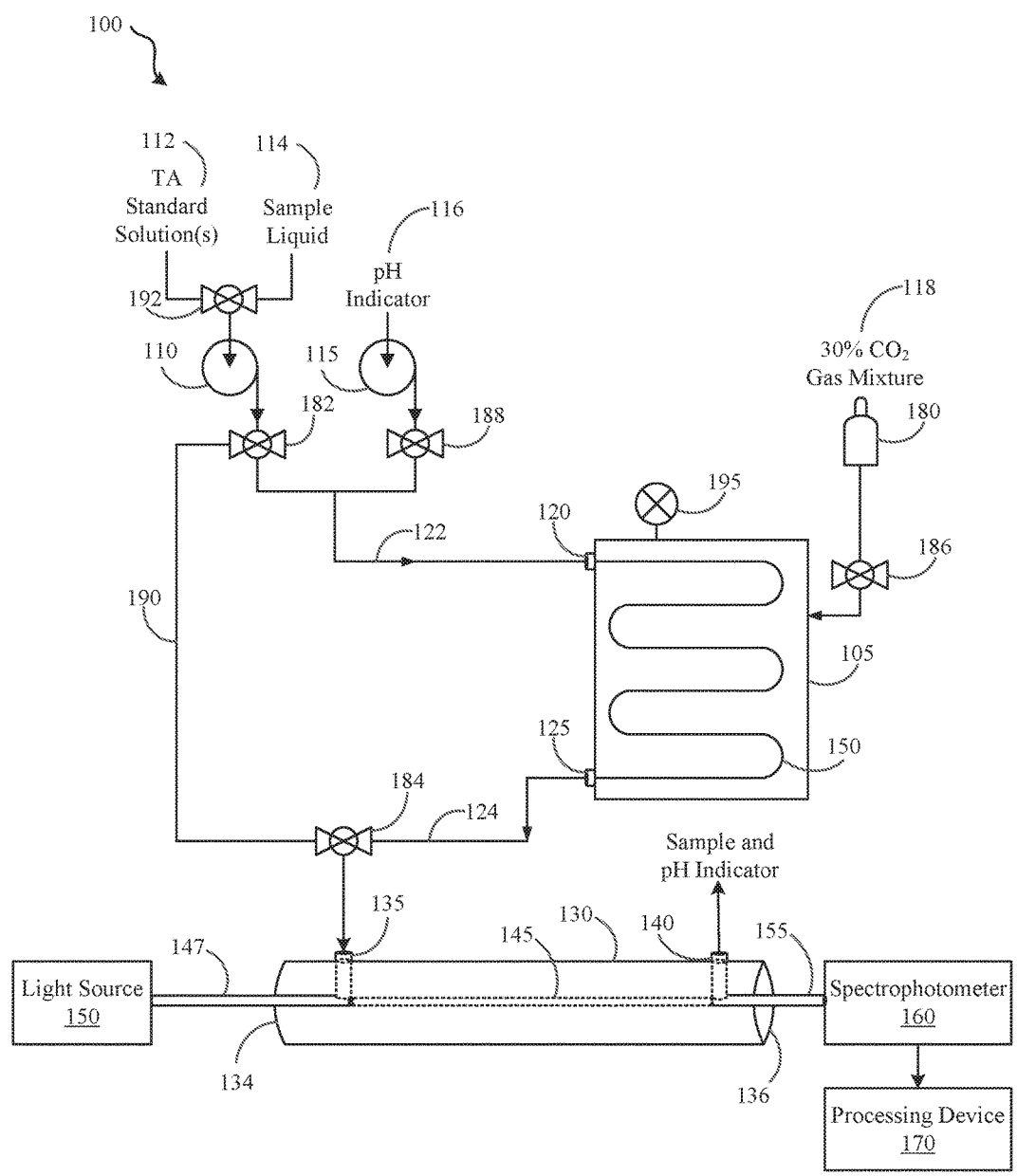
FIG. 1 is block diagram illustrating the system for measuring the total alkalinity of a sample liquid, in accordance with an embodiment of the present invention.

FIG. 1 illustrates an exemplary embodiment of a system 100 used for spectrophotometric measurements of total alkalinity of a sample liquid, in accordance with the present invention. In the embodiment illustrated in FIG. 1, the total alkalinity measurement system 100 includes an equilibration chamber 105 which includes a $CO_2$ permeable tube 150 positioned within the interior of the equilibration chamber 105. An input 120 of the $CO_2$ permeable tube 150 is coupled to a controlled source 110 for providing either a sample liquid 114 or a standard solution 112, as controlled by a valve 192. The input 120 of the $CO_2$ permeable tube 150 is also coupled to a controlled source 115 providing a pH indicator 116. In a particular embodiment, the controlled source 110 providing the sample liquid 114 or the standard solution 112 may be a pump controlled by a valve 182 to regulate the flow of the sample liquid 114 or the standard solution 112 into the $CO_2$ permeable tube 150 and the controlled source 115 providing the pH indicator may be a pump controlled by a valve 188 to regulate the flow of the pH indicator into the $CO_2$ permeable tube 150.

The total alkalinity measurement system 100 additionally includes, a source 180 controlled by a valve 186 to introduce a gas mixture 118, comprising a predetermined percentage of $CO_2$, into the interior of the equilibration chamber 105 to surround the $CO_2$ permeable tube 150. The partial pressure or fugacity of the $CO_2$ is known, and in a particular embodiment, the $CO_2$ concentration of the gas mixture 118 may be about 30%. In this way, a stream of gas from the controlled source 180, having a known $CO_2$ mole fraction, is introduced into the interior of the equilibration chamber 105 and the $CO_2$ is allowed to equilibrate within the equilibration chamber 105. The equilibration chamber 105 may further include a pressure gauge 195 positioned to monitor the internal pressure inside the equilibration chamber 105. As such, the partial pressure or fugacity of the $CO_2$ within the equilibration chamber 105 is known and can be used for the subsequent calculation of the total alkalinity (TA).

In operation of the present invention, the valve 192 is positioned to select the sample liquid 114, the valve 182 coupled to the pump 110 supplying the sample liquid 114 is opened and the valve 180 controlling the pH indicator 116 is opened, thereby allowing the sample liquid 114 and the pH indicator 116 to mix and form a sample solution 122. The sample solution is then introduced at an input 120 into the $CO_2$ permeable gas tube 150 positioned within the interior of the equilibration chamber 105. The valve 186 controlling the gas mixture 118 is also opened and the gas mixture 118 having a known partial pressure of $CO_2$ is introduced into the interior of the equilibration chamber 105. The sample solution 122 is then allowed to equilibrate with the $CO_2$ in the gas mixture until the sample solution is a $CO_2$ equilibrated sample solution having substantially the same partial pressure as the $CO_2$ surrounding the $CO_2$ gas permeable tube in the equilibration chamber. As such, the $CO_2$ partial pressure of the liquid sample is established using a stream of gas, having a known $CO_2$ mole fraction that equilibrates with the sample solution as it flows through the $CO_2$ permeable gas tube 150. The length of the $CO_2$ permeable gas tube 150 is sufficient to allow for the equilibration of the sample solution as it is pumped through the $CO_2$ permeable gas tube 150. In a particular embodiment, the $CO_2$ permeable gas tube 150 is 2-m in length and is a gas-permeable silicon tube that is coiled inside the equilibration chamber 105.

Following equilibration, the $CO_2$ equilibrated sample solution 124 is then introduced at an input 135 of an optical cell 130 through an output 125 of the $CO_2$ permeable gas tube 150, controlled by a valve 184.

In one embodiment, the optical cell 130 includes a first optical fiber 147 positioned partially within an interior of a polyether ether ketone (PEEK) cell casing at a first end 134 of the casing 130 and a second optical fiber 155 positioned partially within the interior of the cell optical cell 130 at a second end 136 of the optical cell 130. The first optical fiber 147 is substantially aligned with the second optical fiber 155. An optical channel 145 is formed within the optical cell 130, such as a bore hole, to allow the equilibrated sample solution 124 to flow through the optical cell 130. A light source 150 is coupled to the first optical fiber 147 and a spectrophotometer 160 is coupled to the second optical fiber 155. The spectrophotometer is coupled to a processing device 170. PEEK is known in the art as an organic thermoplastic polymer in the polyaryletherketone (PAEK) family, which is commonly used in engineering applications.

The optical cell 130 is configured to measure an absorbance ratio of the pH indicator in the equilibrated sample solution 124 at a plurality of frequencies, using the light source 150 and the spectrophotometer 160. The processing device 170 is configured to calculate a total alkalinity of the liquid sample using the absorbance ratio measurements of pH indicator in the equilibrated sample solution and the known partial pressure of the $CO_2$. The processing device 170 may be any one of a variety of custom-designed electronics providing instrument control and data processing that automates many of the process that would normally be performed manually, such as a microcontroller comprising firmware and/or software for automation of the equilibration and TA measurement processes. Since the fugacity of the $CO_2$ ($fCO_2$) of the sample solution with the $CO_2$ permeable tube and the gas surround the tube are identical at equilibrium, the total alkalinity (TA) of the liquid sample inside the $CO_2$ permeable tube can be calculated from known thermodynamic relationships. Using the processing device 170, the total alkalinity (TA) of the sample solution is calculated from the measured absorbance ratios according to the equation:

$$\log(TA+[H^+])=\log(K_0K_1/K_I)+\log pCO_2+\log[(R-e_1)/(e_2-Re_3)]$$

where;

$K_0$ is the Henry's law gas solubility constant, $K_1$ is a carbonic acid dissociation constant, $K_I$ is the pH indicator dye dissociation constant, $pCO_2$ is the known partial pressure of the $CO_2$, R is the measured absorbance ratio, and $e_1$ and $e_2$ and $e_3$ are molar absorptivity ratios appropriate to the pH indicator.

As such, in the present invention, the $CO_2$ partial pressure of the liquid sample at equilibrium is determined from the $CO_2$ mole fraction of the gas and the measured total pressure in the equilibration chamber 105. The total alkalinity measurement system of the present invention can achieve measurement precisions on the order of 1 micromole/kg. With a $CO_2$ partial pressure on the order of 0.30, the final pH of the equilibrated sample solution is on the order of 5.3 or less, in which case effectively all of the sample solution is in the form of bicarbonate. As such, the total alkalinity (TA) of the liquid sample can be measured using the above referenced formula. The system of the present invention allows for equilibration and continuous measurements of TA.

In accordance with the TA measurement system of the present invention, substantially continuous TA measurements of the liquid sample can be performed in the optical cell 130 as the flow of the liquid sample is being equilibrated in the equilibration chamber 105.

In a particular embodiment, the liquid sample may be seawater. However, this is not meant to be limiting and other liquid samples are within the scope of the present invention.

In a particular embodiment, the pH indicator is bromocresol purple (BCP). This indicator has been used for laboratory measurements of seawater alkalinity with a precision better than ±1 μmol kg$^{-1}$. The absorbance characteristics and dissociation behavior of BCP has been measured in both freshwater and seawater media. With an indicator $pK_I$ near 5.8 in seawater media, BCP is ideally suited for pH measurements between 5 and 6.

The optical cell 130 further includes an output 140 for releasing the sample solution from the optical cell 130 after the total alkalinity measurements and calculations have been performed for the sample solution.

In order to provide a baseline for the TA measurements of the liquid solution, in one embodiment, a baseline TA measurement of the liquid solution is performed without the addition of the pH indicator dye. In this embodiment, the liquid sample is provided directly to the optical cell 130 through bypass tubing 190 that does not pass through the equilibration chamber 105.

In order to calibrate the total alkalinity system 100, the system may further include a controlled source 112 of a total alkalinity standard solution that may be provided to the optical cell 130 through a valve 192. The total alkalinity standard solution is a solution (or solutions) of known total alkalinity (TA). The TA values of such solutions can be measured independently using conventional titration procedures, involving the additions of acid to an endpoint, as is known in the art. Alternatively, the total alkalinity solutions can be purchased. In an additional embodiment, the TA of TA standard solutions (which are weakly alkaline) can be measured using the optical cell 130 and can be used to verify that the acid-free TA measurement system of the present invention is performing properly. TA standard solutions can also be used to monitor potential instrumental drift and to correct for any undetected changes in the $CO_2$ partial pressure ($pCO_2$) of the gas that is used for the TA measurements. In a particular embodiment, the TA measurement system could be programmed to autonomously measure the TA of a standard solution after a specified number of TA sample liquid measurements.

In a specific embodiment for measuring the TA of seawater, the TA standard solutions for seawater measurements can be natural seawater solutions that are titrated with acid to determine the TA of the seawater that will be used as a standard. These standards will be quite stable because TA is invariant when $CO_2$ enters or leaves a solution.

In an additional embodiment for measuring the TA of freshwater, the TA standard solutions for freshwater can be generated by simply adding sodium carbonate (Na2CO3) to pure water (along with some amount of sodium chloride, NaCl) to establish the ionic strength of the standard (thereby generating a well-defined ionic medium).

The system for measuring total alkalinity 100 may further include various gas connectors, restrictors and regulators for controlling flow rates, and devices for measuring temperature (air and liquid) and gas pressure.

Figure 2:
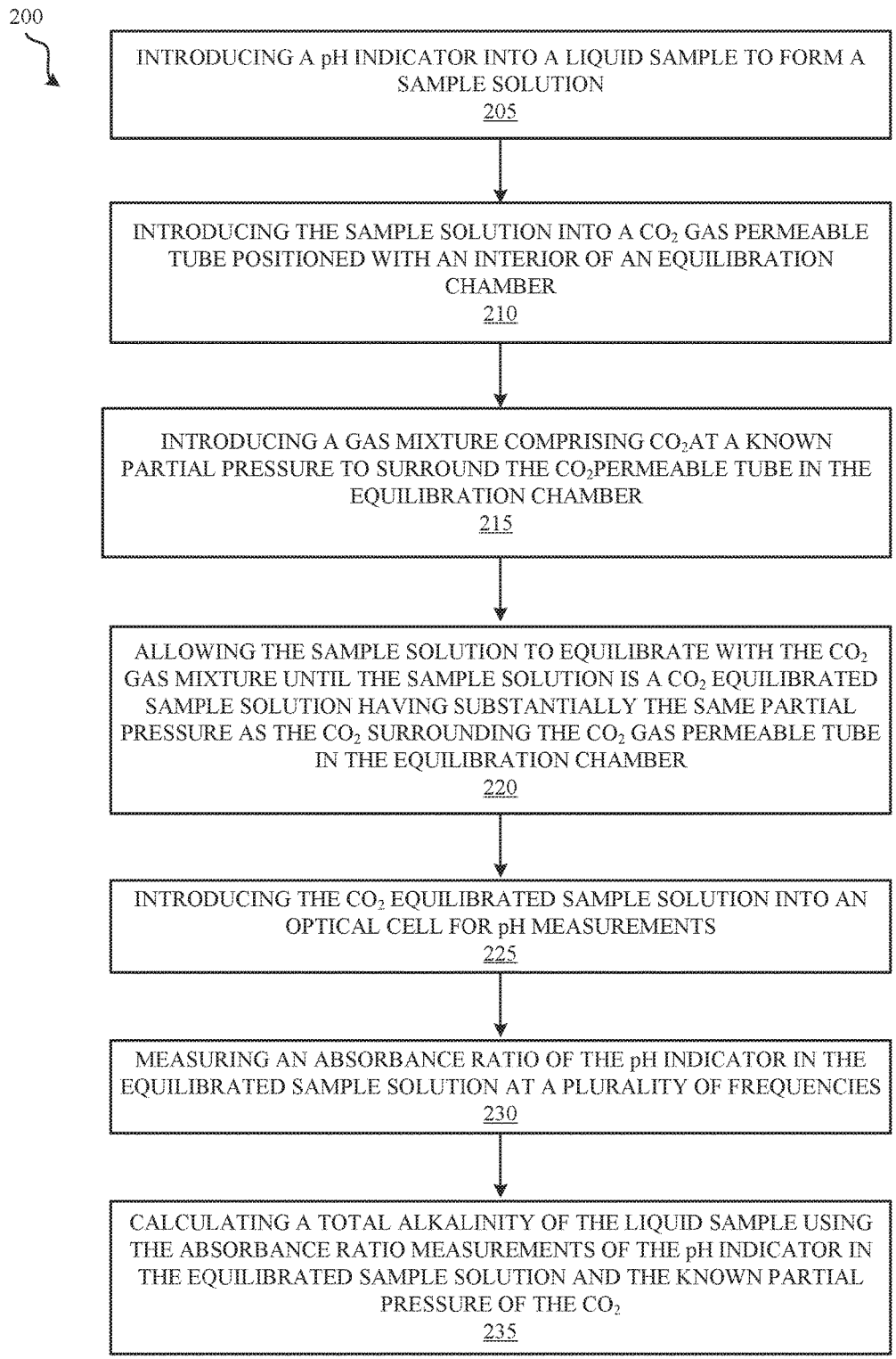
FIG. 2 is a flow diagram illustrating a method for measuring the total alkalinity of a liquid, in accordance with an embodiment of the present invention.

FIG. 2 is a flow diagram illustrating a method for measuring the total alkalinity of a sample solution in accordance with the present invention. With reference to FIG. 2, in accordance with the present invention, a method 200 for measuring the total alkalinity of a sample solution using an equilibration chamber and an optical cell is provided.

As illustrated in FIG. 2, a first step of the inventive method includes, introducing a pH indicator into a liquid sample to form a sample solution 205. As shown with reference to FIG. 1, this method step may be performed by the present invention, wherein the liquid sample 114 may be provided by a pump 110, which is controlled by a valve 182 and the pH indicator may be provided by another pump 115, which is controlled by a valve 188.

Following the formation of the sample solution, the method continues at step 210 of FIG. 2 by introducing the sample solution into a $CO_2$ gas permeable tube positioned within an interior of an equilibration chamber. With reference to FIG. 1, this method step may be performed by the present invention, wherein the sample liquid 114 may be provided at an input 120 to the $CO_2$ gas permeable tube 150 positioned within an interior of an equilibration chamber 105.

Before, after, or substantially simultaneously with the introduction of the sample solution, the method of the present invention continues at step 215 by introducing a gas mixture comprising $CO_2$ at a known partial pressure to surround the $CO_2$ gas permeable tube in the equilibration chamber. As shown in FIG. 1, this method step may be performed by the present invention, wherein the gas mixture 118 may be provided by a controlled source 180 through a valve 186 to provide the gas mixture to the interior of the equilibration chamber 105. The method continues at step 220 by allowing the sample solution 122 consisting of sample liquid 114 and pH indicator 116 to equilibrate with the $CO_2$ in the gas mixture until the sample solution is a $CO_2$ equilibrated sample solution having substantially the same partial pressure as the $CO_2$ surrounding the $CO_2$ gas permeable tube in the equilibration chamber 105.

Following the equilibration of the sample solution, the method continues at step 225 by introducing the $CO_2$ equilibrated sample solution into an optical cell. As shown in FIG. 1, this method step may be performed by the present invention, wherein the $CO_2$ equilibrated sample solution 124 may be provided to an input 135 of the optical cell 130 through an output 125 of the $CO_2$ gas permeable tube 150.

After the equilibrated sample solution has been introduced into the optical cell, the method continues at step 230 by measuring an absorbance ratio of the pH indicator in the equilibrated sample solution at a plurality of frequencies. As shown in FIG. 1, this method step may be performed by the present invention, wherein the light source 150, in combination with the spectrophotometer 160, the first optical fiber 147, the second optical fiber 155 and the optical channel 145, are used to measure the absorbance ratios of the pH indicator in the equilibrated sample solution 124.

After the spectrophotometer measurements have been taken, the method continues at step 235 by calculating a total alkalinity of the liquid sample using the absorbance ratio measurements of the pH indicator in the equilibrated sample solution and the known partial pressure of the $CO_2$ 235. As illustrated in FIG. 1, this method step may be performed by the present invention, wherein the processing device 170 is used to perform the calculations of the total alkalinity (TA) of the sample solution from the measured absorbance ratios according to the equation:

$$\log(TA+[H^+])=\log(K_0 K_1/K_I)+\log pCO_2+\log[(R-e_1)/(e_2-Re_3)]$$

where;

$K_0$ is the Henry's law gas solubility constant, $K_1$ is a carbonic acid dissociation constant, $K_I$ is the pH indicator dye dissociation constant, $pCO_2$ is the known partial pressure of the $CO_2$, R is the measured absorbance ratio, and $e_1$ and $e_2$ and $e_3$ are molar absorptivity ratios appropriate to the pH indicator.

With the system and method of the present invention, the total alkalinity of a sample liquid can be measured by first pre-equilibrating the sample solution and a gas at a chosen $CO_2$ fugacity across a gas permeable membrane. As soon as the solution and $CO_2$ gas are equilibrated, the pH of the solution, such as seawater, is then measured in an optical cell using a spectrophotometric indicator, such as bromocresol purple. $CO_2$ gas, having a known mole fraction, flows outside of the tubing that contains the solution/seawater. In conjunction with measurements of total atmospheric pressure, this allows the $CO_2$ fugacity of the gas to be precisely and accurately calculated. When equilibrium between the solution inside the tubing and the gas outside the tubing has been achieved, and the equilibrium pH of the sample is measured, the total alkalinity (TA) can be calculated. With the partial pressure of $CO_2$ ($pCO_2$) being constant and known, the equilibrium pH measurement allows direct calculation of total alkalinity (TA).

The total alkalinity measurement device of the present invention allows for substantially continuous measurements of total alkalinity without the use of strong acids, and without the use of devices to accurately measure the relative or absolute amounts (volumes) of acids and measured solutions. It is simple, has very few moving parts, and should greatly reduce cost and the need for user expertise.

The present invention provides a field portable device has been developed for high frequency, precise and accurate measurements of total alkalinity. The device is suitable for small boat operations, measurements on shorelines and work in the laboratory.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for determining total alkalinity of a liquid sample, the method comprising:
   introducing a pH indicator into a liquid sample to form a sample solution;
   introducing the sample solution into a $CO_2$ gas permeable tube positioned within an interior of an equilibration chamber;
   introducing a gas mixture comprising $CO_2$ at a known partial pressure to surround the $CO_2$ gas permeable tube in the equilibration chamber;
   allowing the sample solution to equilibrate with the $CO_2$ in the gas mixture until the sample solution is a $CO_2$ equilibrated sample solution having substantially the same partial pressure as the $CO_2$ surrounding the $CO_2$ gas permeable tube in the equilibration chamber;
   introducing the $CO_2$ equilibrated sample solution into an optical cell, wherein the $CO_2$ equilibrated sample solution is provided via an output of the $CO_2$ gas permeable tube in the equilibration chamber to an input of the optical cell;
   measuring an absorbance ratio of the pH indicator in the equilibrated sample solution at a plurality of frequencies; and
   calculating a total alkalinity of the liquid sample using the absorbance ratio measurements of the pH indicator in the equilibrated sample solution and the known partial pressure of the $CO_2$.

2. The method of claim 1, wherein the pH indicator is a sulfonephthalein pH indicator.

3. The method of claim 1, wherein the liquid sample is seawater.

4. The method of claim 1, further comprising determining a baseline total alkalinity of a liquid sample, wherein the determining the baseline total alkalinity of the liquid sample comprises:

introducing the liquid sample without a pH indicator into the optical cell;

measuring an absorbance ratio in the liquid sample without the pH indicator at a plurality of frequencies; and calculating the baseline total alkalinity of the liquid sample using the absorbance ratio measurements of the liquid sample.

5. The method of claim 1, further comprising determining a total alkalinity of total alkalinity standard solutions, wherein the determining a total alkalinity of total alkalinity standard solutions comprises:

introducing a pH indicator into a standard solution having a known total alkalinity to form a standard solution sample;

introducing the standard solution sample into the optical cell;

measuring an absorbance ratio in the standard solution at a plurality of frequencies;

calculating a total alkalinity of the standard solution.

6. The method of claim 1, wherein the gas mixture comprises approximately 30% $CO_2$.

7. The method of claim 1, wherein the introducing a gas mixture comprising $CO_2$ at a known partial pressure to surround the $CO_2$ gas permeable tube in the equilibration chamber further comprises introducing the gas mixture having a known $CO_2$ mole fraction at a controlled rate.

8. The method of claim 1, wherein the $CO_2$ known partial pressure is on the order of 0.30.

9. The method of claim 1, wherein calculating a total alkalinity of the liquid sample using the absorbance ratio measurements of the pH indicator in the equilibrated sample solution and the known partial pressure of the $CO_2$ according to the equation:

$$\log(TA+[H^+])=\log(K_0K_1/K_I)+\log pCO_2+\log[(R-e_1)/(e_2-Re_3)]$$

where;

$K_0$ is the Henry's law gas solubility, $K_1$ is a carbonic acid dissociation constant, $K_I$ is the pH indicator dissociation constant, $pCO_2$ is the known partial pressure of the $CO_2$, R is the measured absorbance ratio, and $e_1$ and $e_2$ and $e_3$ are molar absorptivity ratios appropriate to the pH indicator.

10. A system for determining total alkalinity of a liquid sample, the system comprising:

an equilibration chamber;

a controlled source of a gas mixture comprising $CO_2$ at a known partial pressure coupled to the equilibration chamber;

a $CO_2$ gas permeable tube positioned within an interior of the equilibration chamber;

a controlled source of a liquid sample coupled to an input of the $CO_2$ gas permeable tube;

a controlled source of a pH indicator coupled to an input of the $CO_2$ gas permeable tube;

an output of the $CO_2$ gas permeable tube coupled to an input of an optimal cell;

an optical cell for measuring an absorbance ratio of the pH indicator in an equilibrated sample solution, provided from the output of the $CO_2$ gas permeable tube to the input of the optical cell, at a plurality of frequencies; and a processing device for calculating a total alkalinity of the liquid sample using the absorbance ratio measurements of the pH indicator in the equilibrated sample solution.

11. The system of claim 10, wherein the pH indicator is a sulfonephthalein pH indicator.

12. The system of claim 10, wherein the liquid sample is seawater.

13. The system of claim 10, further comprising a controlled source of a standard solution coupled to the optical cell, the standard solution for performing calibration of the system.

14. The system of claim 13, wherein the controlled source of the liquid sample, the controlled source of the pH indicator and the controlled source of the standard solution comprises a pump and a valve.

15. The system of claim 10, wherein the system further comprises:

a first optical fiber positioned partially within the optical cell;

a light source coupled to a first end of the first optical fiber;

a second optical fiber positioned partially within the optical cell;

an optical channel positioned between a second end of the first optical fiber and a first end of the second optical fiber;

a spectrophotometer coupled to a second end of the second optical fiber; and a processing device coupled to the spectrophotometer.

16. The system of claim 10, wherein the source of a liquid sample is further coupled to the optical cell and wherein the optical cell is further for measuring absorbances of the liquid sample without the pH indicator and the processing device is further for calculating a baseline for total alkalinity measurements of the liquid sample.

17. The system of claim 10, wherein the gas mixture comprises approximately 30% $CO_2$.

18. The system of claim 10, wherein the $CO_2$ known partial pressure is on the order of 0.30.

19. The system of claim 10, wherein the processing device further comprises software for calculating total alkalinity of the liquid samples using the absorbance ratio measurements of the equilibrated sample solution and the known partial pressure of the $CO_2$ according to the equation:

$$\log(TA+[H^+])=\log(K_0K_1/K_I)+\log pCO_2+\log[(R-e_1)/(e_2-Re_3)]$$

$K_0$ is the Henry's law gas solubility constant, $K_1$ is a carbonic acid dissociation constant, $K_I$ is the pH indicator dissociation constant, $pCO_2$ is the known partial pressure of the $CO_2$, R is the measured absorbance ratio, and $e_1$ and $e_2$ and $e_3$ are molar absorptivity ratios appropriate to the pH indicator.

20. A method for determining total alkalinity of a liquid sample, the method comprising:

introducing a pH indicator into a liquid sample to form a sample solution;

introducing the sample solution into a $CO_2$ gas permeable tube positioned within an interior of an equilibration chamber;

introducing a gas mixture comprising $CO_2$ at a known partial pressure to surround the $CO_2$ gas permeable tube in the equilibration chamber;

allowing the sample solution to equilibrate with the $CO_2$ in the gas mixture until the sample solution is a $CO_2$ equilibrated sample solution having substantially the same partial pressure as the $CO_2$ surrounding the $CO_2$ gas permeable tube in the equilibration chamber;

introducing the $CO_2$ equilibrated sample solution into an optical cell, wherein the CO2 equilibrated sample solution is provided via an output of the $CO_2$ gas permeable tube in the equilibration chamber to an input of the optical cell;

measuring an absorbance ratio of the pH indicator in the equilibrated sample solution at a plurality of frequencies;

calculating a total alkalinity of the liquid sample using the absorbance ratio measurements of the pH indicator of the equilibrated sample solution and the known partial pressure of the $CO_2$ according to the equation:

$$\log(TA+[H^+]) = \log(K_0 K_1/K_I) + \log pCO_2 + \log[(R-e_1)/(e_2-Re_3)]$$

$K_0$ is the Henry's law gas solubility constant, $K_1$ is a carbonic acid dissociation constant, $K_I$ is the pH indicator dissociation constant, $pCO_2$ is the known partial pressure of the $CO_2$, R is the measured absorbance ratio, and $e_1$ and $e_2$ and $e_3$ are molar absorptivity ratios appropriate to the pH indicator.

* * * * *